(12) United States Patent
Edupuganti et al.

(10) Patent No.: US 9,296,806 B2
(45) Date of Patent: Mar. 29, 2016

(54) PROCESSES FOR REFOLDING OF INSULIN

(75) Inventors: B Raju Edupuganti, Aurangabad (IN);
Haseeb Jagirdar, Aurangabad (IN);
Manish Kumar, Aurangabad (IN);
Jayaraman Parthipan, Pondicherry (IN); Vivek Yadav, Aurangabad (IN);
Maharaj K Sahib, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 828 days.

(21) Appl. No.: 12/990,352

(22) PCT Filed: Apr. 30, 2009

(86) PCT No.: PCT/IB2009/051763
§ 371 (c)(1),
(2), (4) Date: Mar. 10, 2011

(87) PCT Pub. No.: WO2009/133529
PCT Pub. Date: Nov. 5, 2009

(65) Prior Publication Data
US 2011/0152507 A1    Jun. 23, 2011

(30) Foreign Application Priority Data

Apr. 30, 2008   (IN) ............................ 954/MUM/2008
Apr. 30, 2008   (IN) ............................ 955/MUM/2008
Jul. 18, 2008    (IN) ......................... 1518/MUM/2008

(51) Int. Cl.
*C07K 14/62*    (2006.01)
(52) U.S. Cl.
CPC ..................................... *C07K 14/62* (2013.01)

(58) Field of Classification Search
None
See application file for complete search history.

(56) References Cited

U.S. PATENT DOCUMENTS 5,473,049 A * 12/1995 Obermeier et al. ........... 530/303
5,663,291 A *  9/1997 Obermeier et al. ........... 530/303
6,380,355 B1    4/2002 Rubroder et al.

FOREIGN PATENT DOCUMENTS

RU          2141531 C1    11/1999

OTHER PUBLICATIONS

Winter Jeannette et al: "Ranaturation of Human Proinsulin: A study on Reforlding and Conversion to Insulin." Analytical Biochemistry. vol. 310, No. 2, Nov. 1, 2002.

* cited by examiner

*Primary Examiner* — Amber D Steele
*Assistant Examiner* — Schuyler Milton
(74) *Attorney, Agent, or Firm* — Bio Intellectual Property Services (Bio IPS) LLC; O. (Sam) Zaghmout (57) ABSTRACT

The invention provides processes for obtaining a precursor for insulin, analogs or derivatives thereof having correctly bonded cystine bridges. The process involves solubilizing a precursor of insulin, insulin analog or derivatives in an aqueous solution or a buffer containing cysteine or cysteine hydrochloride and one or more of chaotropic auxiliary. The solubilized precursors are refolded by adding diluent to the solubilized mixture (reverse dilution). Further, the solubilized precursors, wherein the concentration of precursor in reaction mixture is more than 0.65 g/liter can also be refolded by diluting the reaction mixture with a diluent optionally comprising about 5-40% v/v of one or more of alcoholic or aprotic solvents.

16 Claims, 1 Drawing Sheet

PROCESSES FOR REFOLDING OF INSULIN

FIELD OF THE INVENTION

The invention relates to processes for obtaining a precursor of insulin, insulin analogues or derivatives thereof having correctly bonded cystine bridges. The process includes solubilizing a proinsulin precursor having incorrectly bonded cystine bridges in an aqueous solution or a buffer containing one or both of cysteine or cysteine hydrochloride and one or more of chaotropic auxiliaries. The solubilized precursors are then refolded by adding a diluent to the solubilized mixture (reverse dilution). Further, the solubilized precursors, wherein the precursor concentration is more than 0.65 g/liter, can also be refolded by diluting the reaction mixture with a diluent optionally containing about 5-40% v/v of one or more of alcoholic or aprotic solvents.

BACKGROUND OF THE INVENTION

Figure 1:
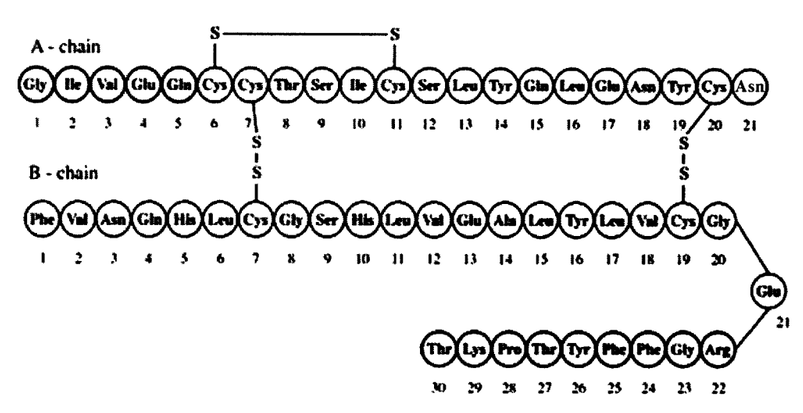
FIG. 1. Insulin is a protein hormone consisting of an acid A-chain of 21 amino acid residues and a basic B-chain of 30 amino acids. A chain and B chain are bonded together by six cysteine residues forming three disulfide bond between following positions: A 6-A 11; A 7-B 7; A 20-B 19.

Insulin is a protein hormone consisting of an acid A-chain of 21 amino acid residues and a basic B-chain of 30 amino acids. A chain and B chain are bonded together by six cysteine residues forming three disulfide bond between following positions: A 6-A 11; A 7-B 7; A 20-B 19 (FIG. 1).

The three-disulfide bonds are important in maintaining the native conformation and biological activities of the insulin molecule. Insulin folds into a unique three-dimensional structure mainly composed of three $\alpha$-helical segments (A2-A8, A13-A19, and B9-B19) stabilized by its three disulfides bonds.

Insulin analogues and derivatives differ from human insulin at one or more than one amino acid positions and/or amino acid chain length.

Insulin, Insulin analogues and derivatives are prepared using recombinant DNA technology in *E. Coli* or yeast. When *E. Coli* is used as host cell, insulin expressed will not be in native soluble and biologically active conformation. Instead of native protein, inactive inclusion bodies accumulated in host cell. These inclusion bodies contain recombinant protein in a highly enriched form with incorrect folding. As a consequence, the recombinant protein must be isolated, refolded under suitable conditions, and enzymatically converted to the biologically active insulin.

There are two important issues in recovering active proteins from inclusion bodies. These include:
  (a) Solubilization of proinsulins, and
  (b) Refolding of proinsulins.

The chaotropic agents and detergents are commonly used as solubilizing agents. They act as protein denaturant. The chaotropic agents break hydrogen bridges in solution, thus disrupting the inter-molecular and intra-molecular interactions with partial or complete unfolding of the protein structure.

A key to the solubilization process is the addition of a reducing agent to maintain cysteine residues in the reduced state and thus prevent non-native intra- and inter-disulphide formation in highly concentrated protein solutions at alkaline pH.

Refolding is accomplished by removal of excessive denaturants by dilution, buffer exchange, diafiltrations, gel filtration chromatography or immobilization onto the solid support. Because of its simplicity, dilution is usually preferred for industrial scale refolding of proteins.

The concentration of protein present in a solubilizing mixture containing reducing agent and chaotropic auxiliary plays an important role in deciding the final yield of correctly folded proinsulins. As the protein concentration in solubilizing media containing both is cysteine and chaotropic auxiliary is increased, the probability of aggregation or precipitation of proteins increases due to increased interaction.

The other factor that results in aggregation of protein molecules is the sudden change in denaturant concentration, which forces protein molecules to collapse into compact structure resulting in precipitation or aggregation.

When denaturant is removed during refolding the hydrophobic effect drives the unfolded protein molecule to sequester their hydrophobic groups, leading to aggregation. For industrial application it is desirable to eliminate or minimize the formation of protein aggregates.

U.S. Pat. Nos. 5,663,291; 5,473,049; 5,986,048; 6,380,355 and U.S. Patent Application 20070106063 disclose processes for obtaining a precursor of insulin or an insulin derivatives thereof having correctly bonded.

Winter, J. et al. Renaturation of human proinsulin-a study on refolding and conversion to insulin. Analytical biochemistry (2002), 310 (2), 148-155 discloses refolding of human proinsulin under suitable redox conditions.

SUMMARY OF THE INVENTION

In one general aspect there is provided a process for obtaining a precursor of insulin, insulin analogues or derivatives thereof having correctly bonded cystine bridges, process comprising:
  a. mixing a precursor of insulin, insulin analogues or derivatives thereof having incorrectly bonded cystine bridges with an aqueous solution or a buffer containing both cysteine or cysteine hydrochloride and one or more of chaotropic auxiliaries, at a pH of about 8 to about 11.5 and at a temperature of about 2° C. to about 55° C.;
  b. adding a diluent to the reaction mixture of step (a), at a pH of about 8 to about 11.5 and at a temperature of about 2° C. to about 40° C.; and
  c. isolating the precursor of insulin, insulin analogues and derivatives thereof having correctly bonded cystine bridges.

The term "analogue of human insulin" (and similar expressions) as used herein refers to human insulin in which one or more amino acids have been deleted and/or replaced by other amino acids, including non-codeable amino acids, or human insulin comprising additional amino acids, i.e. more than 51 amino acids.

The term "derivatives of human insulin" (and similar expressions) as used herein refers to human insulin or an analogue thereof in which at least one organic substituent is bound to one or more of the amino acids.

In another general aspect there is provided a process for obtaining a precursor of insulin, insulin analogues or derivatives thereof having correctly bonded cystine bridges, process comprising:
  a. mixing a precursor of insulin, insulin analogues or derivatives thereof having incorrectly bonded cystine bridges with an aqueous solution or a buffer comprising cysteine or cysteine hydrochloride and one or more of chaotropic auxiliaries, at a pH of about 7 to about 11.5 and at a temperature of about 15° C. to about 55° C.; wherein the concentration of precursor is more than 0.65 g/liter,
  b. mixing the reaction mixture of step (a) with a diluent optionally containing of about 5-40% (v/v) of an alcoholic or polar aprotic solvent, at a pH of about 8 to about 11.5 and a temperature of about 2° C. to about 40° C.; and c. isolating the precursor of insulin, insulin analogues and derivatives thereof having correctly bonded cystine bridges.

Embodiments of the process for obtaining the precursor of insulin, insulin analog or derivatives thereof having correctly bonded cystine bridges may include one or more of the following features. The process may further include buffers, solvents, additives, chaotropic auxiliaries, and the like.

The details of one or more embodiments of the inventions are set forth in the description below. Other features, objects and advantages of the inventions will be apparent from the description and claims.

DETAILED DESCRIPTION OF THE INVENTION

The inventors have now discovered that when proinsulin precursor having incorrectly bonded cystine bridges are solubilized in a solution containing both cysteine or cysteine hydrochloride and chaotropic auxiliary and the solubilized precursors are then diluted by adding a diluent into the solubilized mixture (reverse dilution), the process results in an increased yield of the correctly folded proinsulin precursor as a result of reduced forced aggregation. Further, the inventors have surprising found that there is an increase in yield of solubilized insulin precursors when the concentration of insulin precursor is more than 0.65 g/l in solubilization stage due to increased reaction rates. As the yield of these solubilized protein increases, there is subsequent increase in yield of correctly refolded protein when these solubilized proteins are diluted using a refolding buffer optionally containing alcoholic or aprotic solvents.

The processes are industrially scalable and cost effective. The whole process can be carried out in one pot.

The concentration of cysteine or cysteine hydrochloride in step (a) varies from about 20 mM to about 60 mM.

The chaotropic auxiliaries can be selected from the group consisting of ammonium sulfate, guanidine hydrochloride, ethylene carbonate, thiocyanate, dimethyl sulfoxide and urea.

In one of the embodiments, the chaotropic auxiliary is urea or guanidine hydrochloride.

In another embodiment of the invention, the concentration of chaotropic auxiliary is from about 5M to about 10M.

Suitable buffers for carrying out the reaction in step (a) includes one or more of glycine buffer, phosphate buffer, Tris buffer, and Ethanolamine buffer.

In one of the embodiments of the present invention, the buffer is Tris buffer.

Suitable diluent for carrying out the dilution in step (b) includes one or more of water, glycine buffer, phosphate buffer, Tris buffer, and Ethanolamine buffer, $C_1$-$C_4$ alcohol and cystine or cystine hydrochloride solution.

In one of the embodiments of the present invention, the diluent is Tris buffer.

In another embodiment of the invention, the alcoholic or aprotic solvent can be selected from the group consisting of methanol, ethanol, iso-propanol, n-propanol, t-butanol, dimethylsulfoxide, dimethylformamide, N-methylpyrrolidone, tetrahydrofuran, dioxane, and acetonitrile.

In yet another embodiment of the invention, the alcoholic solvent is isopropyl alcohol.

In another embodiment of the invention, the aqueous solution or buffer in step (a) may further comprise one or more of additives.

Suitable additives include ethylenediamine tetraacetic acid, ethyleneglycol tetraacetic acid (EGTA), arginine, methionine, proline, glycine, alanine, sugars, polyols, salts such as ammonium sulphate and magnesium chloride, and cyclodextrins or salts thereof.

In one of the embodiments of the invention, the additive added to the solvent of step (a) is ethylenediaminetetraacetic acid.

In another embodiment of the invention, the temperature of step (a) is in range of about 2° C. to about 25° C.

In another embodiment of the invention, the step (b) is carried out in a temperature range of 2° C. to about 25° C.

In another embodiment of the invention, the step (a) is carried out at pH of about 8 to about 9.5.

In another embodiment of the invention, step (b) is carried out at pH of about 8 to about 9.5.

In one of the embodiments of the invention, the precursor of the insulin or an insulin derivatives thereof, has the sequence according to the formula I wherein $R^2$ is
  a. a hydrogen atom,
  b. an amino acid residue from the group consisting of lysine (Lys) and arginine (Arg), or
  c. a peptide having 2 to 45 amino acid residues, comprising the amino acid residue lysine (Lys) or arginine (Arg) at the carboxyl end of the peptide;

$R^1$ is a phenylalanine residue (Phe) or a covalent bond;

$R^4$ corresponds to position B-3 of human insulin and is an amino acid selected form the group consisting of asparagine, lysine and proline $R^5$—$R^6$—$R^7$ corresponds to position B-28, B-29 and B-30 of the human insulin chain respectively.

$R^5$ can be selected from the group consisting of Asparagine, Lysine, Leucine, proline, valine, aspartic acid, glutamic acid and alanine optionally substituted with an acyl group having at least 10 carbon atoms.

$R^6$ can be selected from the group consisting of lysine, glutamic acid and proline optionally substituted with an acyl group having at least 10 carbon atoms.

$R^7$ can be selected from the group consisting of threonine, des threonine, alanine, and serine.

(B2 and B4-B27) are the amino acid residues in the positions B2, B4 to B27 of the B chain of human insulin, animal insulin or an insulin derivative thereof;

X is
  i. an amino acid residue from the group consisting of lysine (Lys) and arginine (Arg), or
  ii. a peptide having 2 to 35 amino acid residues, comprising the amino acid residue lysine (Lys) or arginine (Arg) at the N-terminal and at the carboxyl end of the peptide, or
  iii. a peptide having 2 to 35 genetically encodable amino acids, comprising 1 to 5 histidine residues;

(A2-A20) are the amino acid residues in the positions A2 to A20 of the A chain of human insulin, animal insulin or an insulin derivatives thereof; and $R^3$ is a genetically encodable amino acid residue.

The amino acid sequence of peptides and proteins is indicated from N-terminal end of the amino acid chain onward. The details in Formula I in brackets, e.g. A6, A20, B2, B4, B7 or B19, correspond to the position of amino acid residues in the A or B chains of the insulin.

The term "genetically encodable amino acid residue" represents the amino acids Gly, Ala, Ser, Thr, Val, Leu, Ile, Asp, Asn, Glu, Gln, Cys, Met, Arg, Lys, His, Tyr, Phe, Trp, Pro and selenocysteine.

The terms "residues A2-A20" and "residues B2-B29" of "animal insulin" are understood as meaning, for example, the amino acid sequences of insulin from cattle, pigs or chickens. The terms "residues A2-A20" and "B2-B29" of insulin derivatives represent the corresponding amino acid sequences of human insulin, which are formed by the replacement of amino acids by other genetically encodable amino acids.

The A chain of human insulin has the following sequence (SEQ ID NO: 1):

Gly Ile Val Glu Gln Cys Cys Thr Ser Ile Cys Ser

Leu Tyr Gln Leu Glu Asn Tyr Cys Asn.

The B chain of human insulin has the following sequence (SEQ ID NO: 2):

Phe Val Asn Gln His Leu Cys Gly Ser His Leu Val

Glu Ala Leu Tyr Leu Val Cys Gly Glu Arg Gly Phe

Phe Tyr Thr Pro Lys Thr.

The process according to the invention is particularly suitable for obtaining a precursor of insulin or an insulin derivative having the Formula I, whose cystine bridges (not shown in Formula I) are correctly folded, in which $R^2$ is
a) a hydrogen atom, or
b) a peptide having 2 to 15 amino acid residues, at whose carboxyl end is found an arginine residue (Arg);

$R^1$ is a phenylalanine residue (Phe);
$R^4$ is asparagine or lysine;
$R^5$ is lysine, proline, glutamic acid or aspartic acid;
$R^6$ is lysine, proline, glutamic acid optionally substituted with an acyl group having at least 10 carbon atoms;
$R^7$ is threonine or des threonine;
(B2 and B4-B27) are the amino acid residues in the positions B2, B4 to B27 of the B chain of human insulin;
X is the amino acid residue arginine (Arg) or a peptide having 2 to 35 amino acid residues, where at the beginning and at the end of the peptide there are two basic amino acid residues, in particular arginine (Arg) and/or lysine (Lys);

The residue Z which codes for extra amino acid in B-chain of the insulin or insulin analogues or derivatives thereof, as a rule, is part of X in the amino acid sequence of the precursor of Formula I.

(A2-A20) are the amino acid residues in the positions A2 to A20 of the A chain of human insulin; and
$R^3$ is the amino acid residue asparagine (Asn), serine (Ser) or glycine (Gly).

In insulin glargine, $R^3$ in Formula I is glycine (Gly), $R^1$ is phenylalanine (Phe), $R^4$ is asparagine, $R^5$ is proline, $R^6$ is lysine, $R^7$ is threonine and Z is an arginine residue (Arg), or a peptide residue Arg-Arg-OH.

In Insulin Lispro, $R^3$ in Formula I is Asparagine (Asn), $R^1$ is phenylalanine (Phe), $R^4$ is asparagine, $R^5$ is lysine, $R^6$ is proline, $R^7$ is threonine.

The process of present invention can be performed in one pot. The precursor of insulin, insulin analog or derivatives thereof having correctly bonded cystine bridges can be obtained by adding the precursor of insulin, insulin analog or derivatives thereof having incorrectly bonded cystine bridges in a pot. An aqueous solution or a buffer containing cysteine or cysteine hydrochloride and one or more chaotropic auxiliaries is added to the pot containing precursor, at a pH of about 7 to about 11.5 and at a temperature of about 15 to about 55° C. After approximately 4 h, a diluent is slowly added to the pot containing reaction mixture at a pH of about 8 to about 11.5 and a temperature of about 2° C. to about 40° C. The diluted reaction mixture is stirred for about 24 h. After 24 h, precursor of insulin, insulin analogues and derivatives thereof having correctly bonded cystine bridges is then isolated from the reaction mixture.

The precursor of Formula I can be produced in microorganism with the aid of a genetic construct, which are expressed in *Escherichia coli* or *Streptomycetes* during fermentation using the process known in the art.

The invention is further illustrated by the following examples which are provided merely to be exemplary of the invention and do not limit the scope of the invention. Certain modifications and equivalents will be apparent to those skilled in the art and are intended to be included within the scope of the invention.

EXAMPLE 1

Quantification of Insulin Precursor in Inclusion Bodies

After completion of fermentation, the cells were separated off by centrifugation and disrupted by customary high-pressure homogenization. The fusion protein inclusion bodies released were isolated by centrifugation. The isolated inclusion bodies having proinsulin sequence were freeze-dried. Quantity of insulin precursor in inclusion bodies was determined by HPLC.

100 mg of inclusion bodies were dissolved in 100 ml of a solution of 8 M urea containing 100 mm Dithiothreitol. The solution was mixed properly and then heated at 95° C. for 5 min. The solution was centrifuged for 10 min at 10000 rpm and 0.002 ml was applied on to a HPLC column for quantification.

Analytical HPLC Conditions:
Flow rate: 1 ml/min
UV detection: 214 nm
Column: Waters Spherisorb C 18, 4.6×250 mm 5 micron 120 A
Buffer A: 90% water, 10% acetonitrile and 0.1% TFA
Buffer B: 20% Water, 80% acetonitrile and 0.15 TFA
Column temperature: 40° C.
Column equilibrated with 10% buffer B prior to injection of the sample.
Gradient elution starts after 2 min of injection and increase to 100% B in 25 minutes.
Total analysis time was 30 min.

EXAMPLE 2

Process for Obtaining a Precursor of Insulin Whose Cystine Bridges are Correctly Folded The expressed fusion protein as insoluble inclusion bodies having the proinsulin sequence 1 (SEQ ID NO: 3) was collected from *E. coli* cells.

```
Proinsulin sequence 1
                                                 (SEQ ID NO: 3)
Ala Thr Thr Ser Thr Gly Asn Ser Ala Arg Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn X is C-peptide from human insulin;
                                                 (SEQ ID NO: 4)
Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg.
```

EXAMPLE 2A

Refolding by Forward Dilution 480 g of Urea, 9.08 g of L-cysteine hydrochloride and 0.75 g of ethylenediaminetetraacetic acid disodium salt was added to one liter of 20 mM Tris buffer and the pH of the solution was adjusted to 8.5 with 5N sodium hydroxide solution. This solution was poured in a pot. An amount equal to 40 g of isolated freeze dried inclusion bodies containing 16 g of insulin precursor of proinsulin sequence 1 (SEQ ID NO: 3) (the portion of insulin contain fusion protein was determined with the aid of HPLC, it was 40%) was weighed and dissolved in the above solution containing both L-cysteine and urea. The solution was stirred for one hour at room temperature. The pH of the solution was adjusted to 10.6 with 5N sodium hydroxide and the stirring was continued further for 1 h at room temperature. The solubilized mixture was slowly added to 29 liters of precooled (10±2° C.) Tris buffer (20 mM) containing 2 mM EDTA at pH 10.6. The pH of the reaction mixture was adjusted to 10.6 with 5N sodium hydroxide solution. The diluted refolding mixture was stirred for 24 h. After 24 h, the content of insulin precursor of proinsulin sequence 1 having correctly bonded cystine bridges in the reaction mixture was determined with the aid of HPLC. 8.0 g of correctly folded insulin precursor of proinsulin sequence 1 (corresponding to a recovery of 50%) was recovered.

EXAMPLE 2B

Refolding Following Reverse Dilution 480 g of Urea, 9.08 g of L-cysteine hydrochloride and 0.75 g of ethylenediaminetetra acetic acid disodium salt was added to one liter of 20 mM Tris buffer and the pH of the solution was adjusted to 8.5 with 5N sodium hydroxide solution. This solution was poured in a pot. An amount equal to 40 g of isolated freeze dried inclusion bodies containing 16 g of insulin precursor of proinsulin sequence 1 (the portion of insulin contain fusion protein was determined with the aid of HPLC, it was 40%) was weighed and dissolved in the above solution having both cysteine and urea. The solution was stirred for 1 h at room temperature. The pH of the solution was adjusted to 10.6 with 5N sodium hydroxide and the stirring was continued further for 1 h at room temperature. To the above solubilized mixture 29 liters of precooled (10±2° C.) Tris buffer (20 mM) containing 2 mM EDTA at pH 10.6 was added slowly. The pH of the reaction mixture was adjusted to 10.6 with 5N sodium hydroxide solution. The refolding mixture was stirred for 24 h at (10±2° C.). After 24 h, the content of insulin precursor of proinsulin sequence 1 having correctly bonded cystine bridges in the reaction mixture was determined with the aid of HPLC. 9.83 g of correctly folded insulin precursor of proinsulin sequence 1 (corresponding to a recovery of 61.6%) was recovered.

EXAMPLE 2C

Refolding without IPA 573 g of guanidine hydrochloride, 3.5 g of L-cysteine hydrochloride and 0.75 g of ethylenediamine tetra acetic acid disodium salt was added to one liter of 20 mM Tris buffer and pH of the solution was adjusted to 8.5 with 5N sodium hydroxide solution. This solution was poured in a pot. An amount equal to 8 g of isolated freeze dried inclusion bodies containing 3.2 g of insulin precursor of sequence 3 (SEQ ID NO: 3) (the portion of insulin contain fusion protein is determined with the aid of HPLC, it is 40%) was weighed and dissolved in the above solution having both L-cysteine and guanidine hydrochloride. The solution was stirred for four hours at room temperature and transferred over a period of 4 hrs to 9 Liters of precooled (10±2° C.) 20 mM Tris buffer at pH 9.0 containing 6.7 g EDTA, 1.08 g L-cysteine and 773.79 g of guanidine hydrochloride. The diluted refolding mixture was further stirred for 24 hrs at (10±2° C.). After 24 hrs the content of insulin precursor of sequence 3 having correctly bonded cystine bridges in the reaction mixture was determined with the aid of HPLC 1.12 g of correctly folded insulin precursor of sequence 3 (corresponding to a recovery of 35.02%) was recovered.

EXAMPLE 2D

Refolding with 10% IPA 573 g of guanidine hydrochloride, 3.5 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 8 g of isolated freeze dried inclusion bodies containing 3.2 g of insulin precursor of proinsulin sequence 3 (SEQ ID NO: 3) (the portion of insulin contain fusion protein is determined with the aid of HPLC, it is 40%) was weighed and dissolved in the above solution having both L-cysteine and guanidine hydrochloride. The solution was stirred for four hours at room temperature and transferred over a period of 4 hrs to 9 liters of precooled (10±2° C.) Tris buffer (20 mM) containing 6.7 g EDTA, 1.08 g L-cystine, 773.79 g of guanidine hydrochloride and 1 Liter of Iso-propyl alcohol at pH 9. The diluted refolding mixture was stirred for 24 hrs at (10±2° C.). After 24 hrs, the content of insulin precursor proinsulin sequence 3 having correctly bonded cystine bridges in the reaction mixture was determined with the aid of HPLC 1.39 g of correctly folded insulin precursor of proinsulin sequence 3 (corresponding to a recovery of 43.55%) was recovered.

EXAMPLE 2E

Refolding with 20% IPA 573 g of guanidine hydrochloride, 3.5 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 8 g of isolated freeze dried inclusion bodies containing 3.2 g of insulin precursor of proinsulin sequence 3 (SEQ ID NO: 3) (the portion of insulin contain fusion protein is determined with the aid of HPLC, it is 40%) was weighed and dissolved in the above solution having both L-cysteine and guanidine hydrochloride. The solution was stirred for four hours at room temperature and transferred over a period of 4 hrs to 9 liters of precooled (10±2° C.) Tris buffer (20 mM) containing 6.7 g EDTA, 1.36 g, L-cystine, 773.79 g of guanidine hydrochloride and 2 Liter of Iso-propyl alcohol at pH 9. The diluted refolding mixture was stirred for 24 hrs at (10±2° C.). After 24 hrs, the content of insulin precursor proinsulin sequence 3 having correctly bonded cystine bridges in the reaction mixture was determined with the aid of HPLC. 1.52 g of correctly folded insulin precursor of proinsulin sequence 3 (corresponding to a recovery of 47.64%) was recovered.

EXAMPLE 3

Process for Obtaining a Precursor of Insulin Derivatives, Whose Cystine Bridges are Correctly Folded The expressed fusion protein as insoluble inclusion bodies having the proinsulin sequence 2 (SEQ ID NO: 5) was collected from E. coli cells.

```
Proinsulin sequence 1
                                         (SEQ ID NO: 5)
Ala Thr Thr Ser Thr Gly Asn Ser Ala Arg Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Gly X is C-peptide from human insulin;
                                         (SEQ ID NO: 4)
Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg.
```

EXAMPLE 3A

Refolding by Forward Dilution 480 g of Urea, 9.08 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 40 g of isolated freeze dried inclusion bodies containing 14 g of insulin precursor of proinsulin sequence 2 (SEQ ID NO: 5) (the portion of insulin contain fusion protein is determined with the aid of HPLC, it is 35%) was weighed and dissolved in the above solution having both L-cysteine and urea. The solution was stirred for one hour at room temperature. The pH of the solution was adjusted to 10.6 with 5N sodium hydroxide and the stirring was continued further for 1 h at room temperature. The solubilized mixture was slowly added to 29 liters of precooled (10±2° C.) Tris buffer (20 mM) containing 2 mM EDTA at pH 10.6. The pH of the reaction mixture was adjusted to 10.6 with 5N sodium hydroxide solution. The diluted refolding mixture was stirred for 24 h. After 24 h, the content of insulin precursor proinsulin sequence 2 having correctly bonded cystine bridges in the reaction mixture was determined with the aid of HPLC. 6.74 g of correctly folded insulin precursor of proinsulin sequence 2 (corresponding to a recovery of 48.28%) was recovered.

EXAMPLE 3B

Refolding Following Reverse Dilution 480 g of Urea, 9.08 g of L-cysteine hydrochloride and 0.75 g of ethylenediaminetetra acetic acid disodium salt was added to one liter of 20 mM Tris buffer and the pH of the solution was adjusted to 8.5 with 5N sodium hydroxide solution. This solution was poured in a pot. An amount equal to 40 g of isolated freeze dried inclusion bodies containing 14 g of insulin precursor of proinsulin sequence 2 (SEQ ID NO: 5) (the portion of insulin contain fusion protein is determined with the aid of HPLC, it is 35%) was weighed and dissolved in the above solution containing both L-cysteine and urea. The solution was stirred for 1 h at room temperature. The pH of the solution was raised to 10.6 with 5N sodium hydroxide and the stirring was continued further for 1 h at room temperature. To the above solubilized mixture 29 liters of precooled (10±2° C.) Tris buffer (20 mM) containing 2 mM EDTA at pH 10.6 was added slowly. The pH of the reaction mixture was adjusted to 10.6 with 5N sodium hydroxide solution. The refolding mixture was kept under stirring for 24 h at (10±2° C.). After 24 h, the content of insulin precursor of proinsulin sequence 2 (SEQ ID NO: 5) having correctly bonded cystine bridges in the reaction mixture was determined with the aid of HPLC. 7.7 g of correctly folded insulin precursor of proinsulin sequence 2 (corresponding to a recovery of 55.7%) was recovered.

EXAMPLE 3C

Refolding without IPA 573 g of guanidine hydrochloride, 3.5 g of L-cysteine hydrochloride and 0.75 g of ethylenediamine tetra acetic acid disodium salt was added to one liter of 20 mM Tris buffer and pH of the solution was adjusted to 8.5 with 5N sodium hydroxide solution. This solution was poured in a pot. An amount equal to 8 g of isolated freeze dried inclusion bodies containing 3.2 g of insulin precursor of sequence 5 (SEQ ID NO: 5) (the portion of insulin contain fusion protein is determined with the aid of HPLC, it is 40%) was weighed and dissolved in the above solution having both L-cysteine and guanidine hydrochloride. The solution was stirred for four hours at room temperature and transferred over a period of 4 hrs to 9 Liters of precooled (10±2° C.) 20 mM Tris buffer at pH 9.0 containing 6.7 g EDTA, 1.08 g L-cysteine and 773.79 g of guanidine hydrochloride. The diluted refolding mixture was further stirred for 24 hrs at (10±2° C.). After 24 hrs the content of insulin precursor of sequence 5 having correctly bonded cystine bridges in the reaction mixture was determined with the aid of HPLC 1.1 g of correctly folded insulin precursor of sequence 5 (corresponding to a recovery of 34.5%) was recovered.

EXAMPLE 3D

Refolding with 10% IPA 573 g of guanidine hydrochloride, 3.5 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 8 g of isolated freeze dried inclusion bodies containing 3.2 g of insulin precursor of proinsulin sequence 5 (SEQ ID NO: 5) (the portion of insulin contain fusion protein is determined with the aid of HPLC, it is 40%) was weighed and dissolved in the above solution having both L-cysteine and guanidine hydrochloride. The solution was stirred for four hours at room temperature and transferred over a period of 4 hrs to 9 liters of precooled (10±2° C.) Tris buffer (20 mM) containing 6.7 g EDTA, 1.08 g, L-cystine, 773.79 g of guanidine hydrochloride and 1 Liter of Iso-propyl alcohol at pH 9. The diluted refolding mixture was stirred for 24 hrs at (10±2° C.). After 24 h, the content of insulin precursor proinsulin sequence 5 having correctly bonded cystine bridges in the reaction mixture was determined with the aid of HPLC 1.3 g of correctly folded insulin precursor of proinsulin sequence 5 (corresponding to a recovery of 40.71%) was recovered.

EXAMPLE 3E

Refolding with 20% IPA 573 g of guanidine hydrochloride, 3.5 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 8 g of isolated freeze dried inclusion bodies containing 3.2 g of insulin precursor of proinsulin sequence 5 (SEQ ID NO: 5) (the portion of insulin contain fusion protein is determined with the aid of HPLC, it is 40%) was weighed and dissolved in the above solution having both L-cysteine and guanidine hydrochloride. The solution was stirred for four hours at room temperature and transferred over a period of 4 hrs to 9 liters of precooled (10±2° C.) Tris buffer (20 mM) containing 6.7 g EDTA, 1.36 g L-cystine, 773.79 g of guanidine hydrochloride and 2 Liter of Iso propyl alcohol at pH 9. The diluted refolding mixture was stirred for 24 hrs at (10±2° C.). After 24 h, the content of insulin precursor proinsulin sequence 5 having correctly bonded cystine bridges in the reaction mixture was determined with the aid of HPLC. 1.47 g of correctly folded insulin precursor of proinsulin sequence 5 (corresponding to a recovery of 46.22%) was recovered.

EXAMPLE 4

Process for Obtaining a Precursor of Insulin Analogue, Whose Cystine Bridges are Correctly Folded The expressed fusion protein as insoluble inclusion bodies having the proinsulin sequence 3 (SEQ ID NO: 6) was collected from *E. coli* cells.

```
Proinsulin sequence 1
                                        (SEQ ID NO: 6)
Ala Thr Thr Ser Thr Gly Asn Ser Ala Arg Phe Val Asn Gln His Leu Cys Gly Ser His Leu Val Glu Ala Leu Tyr Leu Val Cys Gly Glu Arg Gly Phe Phe Tyr Thr Lys Pro Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn.

X is C-peptide from human insulin;
                                        (SEQ ID NO: 4)
Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg.
```

EXAMPLE 4A

Refolding by Forward Dilution 480 g of Urea, 9.08 g of L-cysteine hydrochloride and 0.75 g of ethylenediaminetetra acetic acid disodium salt was added to one liter of 20 mM Tris buffer and the pH of the solution was adjusted to 8.5 with 5N sodium hydroxide solution. This solution was poured in a pot. An amount equal to 40 g of isolated freeze dried inclusion bodies containing 14 g of insulin precursor of proinsulin sequence 3 (SEQ ID NO: 6) (the portion of insulin contain fusion protein is determined with the aid of HPLC, it is 35%) was weighed and dissolved in the above solution having both L-cysteine and urea. The solution was stirred for one hour at room temperature. The pH of the solution was adjusted to 10.6 with 5N sodium hydroxide and the stirring was continued further for 1 h at room temperature. The solubilized mixture was slowly added to 29 liters of precooled (10±2° C.) Tris buffer (20 mM) containing 2 mM EDTA at pH 10.6. The pH of the reaction mixture was adjusted to 10.6 with 5N sodium hydroxide solution. The diluted refolding mixture was stirred for 24 h. After 24 h, the content of insulin precursor of proinsulin sequence 3 having correctly bonded cystine bridges in the reaction mixture was determined with the aid of HPLC. 7.14 g of correctly folded insulin precursor of proinsulin sequence 3 (corresponding to a recovery of 51%) was recovered.

EXAMPLE 4B

Refolding Following Reverse Dilution 480 g of Urea, 9.08 g of L-cysteine hydrochloride and 0.75 g of ethylenediaminetetra acetic acid disodium salt was added to one liter of 20 mM Tris buffer and the pH of the solution was adjusted to 8.5 with 5N sodium hydroxide solution. This solution was poured in a pot. An amount equal to 40 g of isolated freeze dried inclusion bodies containing 14 g of insulin precursor of proinsulin sequence 3 (SEQ ID NO: 6) (the portion of insulin contain fusion protein is determined with the aid of HPLC, it is 35%) was weighed and dissolved in the above solution having both L-cysteine and urea. The solution was stirred for 1 h at room temperature. The pH of the solution was adjusted to 10.6 with 5N sodium hydroxide and the stirring was continued further for 1 h at room temperature. To the above solubilized mixture 29 liters of precooled (10±2° C.) Tris buffer (20 mM) containing 2 mM EDTA at pH 10.6 was added slowly. The pH of the reaction mixture was adjusted to 10.6 with 5N sodium hydroxide solution. The refolding mixture was stirred for 24 h at (10±2° C.). After 24 h, the content of insulin precursor of proinsulin sequence 3 having correctly bonded cystine bridges in the reaction mixture was determined with the aid of HPLC. 7.5 g of correctly folded insulin precursor of proinsulin sequence 3 (corresponding to a recovery of 54%) was recovered.

EXAMPLE 4C

Refolding without IPA 573 g of guanidine hydrochloride, 3.5 g of L-cysteine hydrochloride and 0.75 g of ethylenediamine tetra acetic acid disodium salt was added to one liter of 20 mM Tris buffer and pH of the solution was adjusted to 8.5 with 5N sodium hydroxide solution. This solution was poured in a pot. An amount equal to 8 g of isolated freeze dried inclusion bodies containing 2.8 g of insulin precursor of sequence 6 (SEQ ID NO: 6) (the portion of insulin contain fusion protein is determined with the aid of HPLC, it is 35%) was weighed and dissolved in the above solution having both L-cysteine and guanidine hydrochloride. The solution was stirred for four hours at room temperature and transferred over a period of 4 hrs to 9 Liters of precooled (10±2° C.) 20 mM Tris buffer at pH 9.0 containing 6.7 g EDTA, 1.08 g L-cysteine and 773.79 g of guanidine hydrochloride. The diluted refolding mixture was further stirred for 24 hrs at (10±2° C.). After 24 h the content of insulin precursor of sequence 6 having correctly bonded cystine bridges in the reaction mixture was determined with the aid of HPLC 0.793 g of correctly folded insulin precursor of sequence 6 (corresponding to a recovery of 28.34%) was recovered.

EXAMPLE 4D

Refolding with 10% IPA 573 g of guanidine hydrochloride, 3.5 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 8 g of isolated freeze dried inclusion bodies containing 2.8 g of insulin precursor of proinsulin sequence 6 (SEQ ID NO: 6) (the portion of insulin contain fusion protein is determined with the aid of HPLC, it is 35%) was weighed and dissolved in the above solution having both L-cysteine and guanidine hydrochloride. The solution was stirred for four hours at room temperature and transferred over a period of 4 hrs to 9 liters of precooled (10±2° C.) Tris buffer (20 mM) containing 6.7 g EDTA, 1.08 g L-cystine, 773.79 g of guanidine hydrochloride and 1 Liter of Iso-propyl alcohol at pH 9. The diluted refolding mixture was stirred for 24 hrs at (10±2° C.). After 24 h, the content of insulin precursor proinsulin sequence 6 having correctly bonded cystine bridges in the reaction mixture was determined with the aid of HPLC 1.02 g of correctly folded insulin precursor of proinsulin sequence 6 (corresponding to a recovery of 36.58%) was recovered.

EXAMPLE 4E

Refolding with 20% IPA 573 g of guanidine hydrochloride, 3.5 g of L-cysteine hydrochloride and 0.75 g of ethylenediamine tetra acetic acid disodium salt was added to one liter of 20 mM Tris buffer and the pH of the solution was adjusted to 8.5 with 5N sodium hydroxide solution. This solution was poured in a pot. An amount equal to 8 g of isolated freeze dried inclusion bodies containing 2.8 g of insulin precursor of proinsulin sequence 6 (SEQ ID NO: 6) (the portion of insulin contain fusion protein is determined with the aid of HPLC, it is 35%) was weighed and dissolved in the above solution having both L-cysteine and guanidine hydrochloride. The solution was stirred for four hours at room temperature and transferred over a period of 4 hrs to 9 liters of precooled (10±2° C.) Tris buffer (20 mM) containing 6.7 g EDTA, 1.36 g L-cystine, 773.79 g of guanidine hydrochloride and 2 Liter of Iso-propyl alcohol at pH 9. The diluted refolding mixture was stirred for 24 hrs at (10±2° C.). After 24 h, the content of insulin precursor proinsulin sequence 6 having correctly bonded cystine bridges in the reaction mixture was determined with the aid of HPLC. 1.6 g of correctly folded insulin precursor of proinsulin sequence 6 (corresponding to a recovery of 48.65%) was recovered.

While the invention has been described in terms of its specific embodiments, certain modifications and equivalents will be apparent to those skilled in the art and are intended to be included within the scope of the invention.

We claim:

1. A process for obtaining a precursor of insulin, insulin analogues or derivatives thereof having correctly bonded cystine bridges, the process consisting of:
   a) mixing a precursor of insulin, insulin analogues or derivatives thereof having incorrectly bonded cystine bridges with an aqueous solution or a buffer containing about 20 mM to about 60 mM of both cysteine or cysteine hydrochloride and one or more chaotropic auxiliary at a pH of about 8 to about 11.5 and at a temperature of from about 2° C. to about 55° C.; wherein the concentration of precursor in the resulting mixture is from about 0.65 g/l to about 16 g/l;
   b) reverse diluting by slowly adding a diluent to reaction mixture of step (a), at a pH of about 8 to about 11.5 and at a temperature of about 2° C. to about 40° C.; and
   c) isolating the precursor of insulin, insulin analogues or derivatives thereof having correctly bonded cystine bridges,
      wherein the precursor of the insulin or an insulin derivatives thereof has a sequence according to the formula I:

wherein
R² is
   a. a hydrogen atom,
   b. an amino acid residue from the group consisting of lysine (Lys) and arginine (Arg), or
   c. a peptide having 2 to 45 amino acid residues, comprising the amino acid residue lysine (Lys) or arginine (Arg) at the carboxyl end of the peptide;

R¹ is a phenylalanine residue (Phe) or a covalent bond;

R⁴ corresponds to position B-3 of human insulin and is an amino acid selected form the group consisting of asparagine, lysine and proline;

R⁵—R⁶—R⁷ corresponds to position B-28, B-29 and B-30 of human insulin chain, respectively;

R⁵ is selected from the group consisting of asparagine, lysine, leucine, proline, valine, aspartic acid, glutamic acid and alanine optionally substituted with an acyl group having at least 10 carbon atoms;

R⁶ is selected from the group consisting of lysine, glutamic acid and proline optionally substituted with an acyl group having at least 10 carbon atoms;

R⁷ is selected from the group consisting of threonine, des threonine, alanine, and serine; (B2 and B4-B27) are the amino acid residues in the positions B2, B4 to B27 of the B chain of human insulin, animal insulin or an insulin derivative thereof;

X is i. an amino acid residue selected from the group consisting of lysine (Lys) and arginine (Arg), or ii. a peptide having 2 to 35 amino acid residues, comprising the amino acid residue lysine (Lys) or arginine (Arg) at the N-terminal and at the carboxyl end of the peptide, or iii. a peptide having 2 to 35 genetically encodable amino acids, comprising 1 to 5 histidine residues;

(A2-A20) are the amino acid residues in the positions A2 to A20 of the A chain of human insulin, animal insulin or an insulin derivatives thereof; and $R^3$ is a genetically encodable amino acid residue.

2. The process of claim 1, wherein the one or more chaotropic auxiliary are selected from the group consisting of ammonium sulfate, guanidine hydrochloride, ethylene carbonate, thiocyanate, dimethylsulfoxide and urea.

3. The process of claim 2, wherein the concentration of the chaotropic auxiliary varies from about 5M to about 10M.

4. The process of claim 1, wherein the buffer in step (a) is selected from the group consisting of glycine buffer, phosphate buffer, carbonate buffer, tris buffer, and ethanolamine buffer.

5. The process of claim 1, wherein the diluent in step (b) is selected from the group consisting of water, glycine buffer, phosphate buffer, carbonate buffer, tris buffer, ethanolamine buffer, $C_1$-$C_4$ alcohol, cystine and cystine hydrochloride solution.

6. The process of claim 1, wherein the aqueous solution or a buffer in step (a) or diluent in step (b) may further comprise one or more of additives selected from the group consisting of ethylenediamine tetraacetic acid, ethyleneglycol tetraacetic acid (EGTA), arginine, glycine, alanine, sugars, polyols, salts such as ammonium sulfate and magnesium chloride, and cyclodextrins or salts thereof.

7. The process of claim 1, wherein step (a) or step (b) is carried out at a temperature from about 2° C. to about 25° C.

8. A process for obtaining a precursor of insulin, insulin analog or derivatives thereof having correctly bonded cystine bridges, process consisting of:

a. mixing a precursor of insulin, insulin analog or derivatives thereof having incorrectly bonded cystine bridges with an aqueous solution or a buffer comprising about 20 mM to about 60 mM of both cysteine or cysteine hydrochloride and one or more chaotropic auxiliary at a pH of about 7 to about 11.5 and at a temperature of about 2° C. to about 55° C.; wherein the concentration of precursor in the resulting mixture is from about 0.65 g/liter to about 16 g/liter;

b. mixing the reaction mixture of step (a) with a diluent containing about 5-40% (v/v) of an alcoholic or polar aprotic solvent at a pH of about 8 to about 11.5 and at a temperature of about 2° C. to about 40° C.; and c. isolating the precursors of insulin, insulin analogues and derivatives thereof having correctly bonded cystine bridges, wherein the precursor of the insulin or an insulin derivatives thereof has a sequence according to the formula I:

wherein $R^2$ is a. a hydrogen atom, b. an amino acid residue from the group consisting of lysine (Lys) and arginine (Arg), or c. a peptide having 2 to 45 amino acid residues, comprising the amino acid residue lysine (Lys) or arginine (Arg) at the carboxyl end of the peptide;

$R^1$ is a phenylalanine residue (Phe) or a covalent bond;

$R^4$ corresponds to position B-3 of human insulin and is an amino acid selected form the group consisting of asparagine, lysine and proline;

$R^5$—$R^6$—$R^7$ corresponds to position B-28, B-29 and B-30 of human insulin chain, respectively;

$R^5$ is selected from the group consisting of asparagine, lysine, leucine, proline, valine, aspartic acid, glutamic acid and alanine optionally substituted with an acyl group having at least 10 carbon atoms;

$R^6$ is selected from the group consisting of lysine, glutamic acid and proline optionally substituted with an acyl group having at least 10 carbon atoms;

$R^7$ is selected from the group consisting of threonine, des threonine, alanine, and serine; (B2 and B4-B27) are the amino acid residues in the positions B2, B4 to B27 of the B chain of human insulin, animal insulin or an insulin derivative thereof;

X is i. an amino acid residue selected from the group consisting of lysine (Lys) and arginine (Arg), or ii. a peptide having 2 to 35 amino acid residues, comprising the amino acid residue lysine (Lys) or arginine (Arg) at the N-terminal and at the carboxyl end of the peptide, or iii. a peptide having 2 to 35 genetically encodable amino acids, comprising 1 to 5 histidine residues;

(A2-A20) are the amino acid residues in the positions A2 to A20 of the A chain of human insulin, animal insulin or an insulin derivatives thereof; and $R^3$ is a genetically encodable amino acid residue.

9. The process of claim 8, wherein one or more of chaotropic auxiliary are selected from the group consisting of ammonium sulfate, guanidine hydrochloride, ethylene carbonate, thiocyanate, dimethylsulfoxide and urea.

10. The process of claim 9, wherein the concentration of the chaotropic auxiliary varies from about 5M to about 10M.

11. The process of claim 8, wherein the buffer in step (a) is selected from the group consisting of glycine buffer, phosphate buffer, carbonate buffer, tris buffer, and ethanolamine buffer.

12. The process of claim 8, wherein the diluent in step (b) is selected from the group consisting of water, glycine buffer, phosphate buffer, carbonate buffer, tris buffer, ethanolamine buffer, $C_1$-$C_4$ alcohol and cystine and cystine hydrochloride solution.

13. The process of claim 8, wherein the alcoholic or aprotic solvent is selected from the group consisting of methanol, ethanol, isopropanol, n-propanol, t-butanol, dimethylsulfoxide, dimethylformamide, N-methylpyrrolidone, tetrahydrofuran, dioxane, and acetonitrile.

14. The process of claim 13, wherein the alcoholic solvent is isopropyl alcohol.

15. The process of claim 8, wherein the aqueous solution or a buffer in step (a) and diluent in step (b) may further comprise one or more of additives selected from the group consisting of, ethylenediamine tetraacetic acid, ethyleneglycol tetraacetic acid (EGTA), arginine, glycine, alanine, sugars, salts such as ammonium sulphate and magnesium chloride, and cyclodextrins or salts thereof.

16. The process of claim 8, wherein step (a) or step (b) is carried out at a temperature from about 2° C. to about 25° C.

* * * * *

SEQUENCE LISTING

```
<160> NUMBER OF SEQ ID NOS: 6

<210> SEQ ID NO 1
<211> LENGTH: 21
<212> TYPE: PRT
<213> ORGANISM: Homo sapiens
<220> FEATURE:
<221> NAME/KEY: PEPTIDE
<222> LOCATION: (1)..(21)

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
```

-continued

<211> LENGTH: 30
<212> TYPE: PRT
<213> ORGANISM: Homo sapiens
<220> FEATURE:
<221> NAME/KEY: PEPTIDE
<222> LOCATION: (1)..(30)

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 96
<212> TYPE: PRT
<213> ORGANISM: Homo sapiens
<220> FEATURE:
<221> NAME/KEY: PEPTIDE
<222> LOCATION: (1)..(96)

<400> SEQUENCE: 3

Ala Thr Thr Ser Thr Gly Asn Ser Ala Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
        35                  40                  45

Val Gly Gln Val Glu Leu Gly Gly Gly Pro Gly Ala Gly Ser Leu Gln
    50                  55                  60

Pro Leu Ala Leu Glu Gly Ser Leu Gln Lys Arg Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 4
<211> LENGTH: 35
<212> TYPE: PRT
<213> ORGANISM: Homo sapiens
<220> FEATURE:
<221> NAME/KEY: PEPTIDE
<222> LOCATION: (1)..(35)

<400> SEQUENCE: 4

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Gly Ser Leu
            20                  25                  30

Gln Lys Arg
        35

<210> SEQ ID NO 5
<211> LENGTH: 96
<212> TYPE: PRT
<213> ORGANISM: Homo sapiens
<220> FEATURE:
<221> NAME/KEY: PEPTIDE
<222> LOCATION: (1)..(96)

<400> SEQUENCE: 5

Ala Thr Thr Ser Thr Gly Asn Ser Ala Arg Phe Val Asn Gln His Leu
1               5                   10                  15

Cys Gly Ser His Leu Val Glu Ala Leu Tyr Leu Val Cys Gly Glu Arg

```
                     20                  25                  30
Gly Phe Phe Tyr Thr Pro Lys Thr Arg Arg Glu Ala Glu Asp Leu Gln
                35                  40                  45

Val Gly Gln Val Glu Leu Gly Gly Pro Gly Ala Gly Ser Leu Gln
         50                  55                  60

Pro Leu Ala Leu Glu Gly Ser Leu Gln Lys Arg Gly Ile Val Glu Gln
 65                  70                  75                  80

Cys Cys Thr Ser Ile Cys Ser Leu Tyr Gln Leu Glu Asn Tyr Cys Gly
                 85                  90                  95

<210> SEQ ID NO 6
<211> LENGTH: 96
<212> TYPE: PRT
<213> ORGANISM: Homo sapiens
<220> FEATURE:
<221> NAME/KEY: PEPTIDE
<222> LOCATION: (1)..(96)

<400> SEQUENCE: 6

Ala Thr Thr Ser Thr Gly Asn Ser Ala Arg Phe Val Asn Gln His Leu
 1               5                  10                  15

Cys Gly Ser His Leu Val Glu Ala Leu Tyr Leu Val Cys Gly Glu Arg
                 20                  25                  30

Gly Phe Phe Tyr Thr Lys Pro Thr Arg Arg Glu Ala Glu Asp Leu Gln
                35                  40                  45

Val Gly Gln Val Glu Leu Gly Gly Pro Gly Ala Gly Ser Leu Gln
         50                  55                  60

Pro Leu Ala Leu Glu Gly Ser Leu Gln Lys Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95
```